United States Patent
Kimbrell

(10) Patent No.: US 6,299,018 B1
(45) Date of Patent: Oct. 9, 2001

(54) BANDAGE DISPENSING DEVICE

(76) Inventor: Kimberly L. Kimbrell, 3890 Appaloosa Trail, Douglasville, GA (US) 30135

( * ) Notice: Subject to any disclaimer, the term of this patent is extended or adjusted under 35 U.S.C. 154(b) by 0 days.

(21) Appl. No.: 09/405,952

(22) Filed: Sep. 27, 1999

(51) Int. Cl.$^7$ .................................................. B65H 5/28
(52) U.S. Cl. ............................ 221/71; 221/185; 242/597.8
(58) Field of Search .................................... 221/24, 25, 21, 221/72, 73, 74, 185; 206/440, 441, 409, 411; 242/597.8

(56) References Cited

U.S. PATENT DOCUMENTS

| | | | |
|---|---|---|---|
| D. 376,718 | * 12/1996 | Wilcox | ................................. D6/513 |
| 2,464,426 | 3/1949 | Williams . | |
| 3,189,219 | 6/1965 | Holzworth et al. . | |
| 3,219,244 | * 11/1965 | Blask | ..................... 221/185 |
| 3,653,539 | 4/1972 | Stageberg . | |
| 4,088,276 | * 5/1978 | Littleton | ........................ 242/897.8 |
| 4,167,253 | * 9/1979 | Rutz | ....................... 242/598.6 |
| 4,735,342 | 4/1988 | Goldstein . | |
| 4,872,593 | 10/1989 | Behringer . | |
| 4,884,992 | * 12/1989 | Grimes | ..................... 221/24 |
| 4,993,586 | * 2/1991 | Taulbee et al. | ........................ 221/25 |
| 5,065,894 | 11/1991 | Garland . | |
| 5,119,969 | * 6/1992 | Haber | ....................... 221/25 |
| 5,133,477 | 7/1992 | Etheredge, III et al. . | |
| 5,271,522 | 12/1993 | Ko et al. . | |
| 5,354,140 | 10/1994 | Pellegrino . | |
| 5,378,301 | * 1/1995 | Boreali et al. | ......................... 221/73 |
| 5,499,740 | 3/1996 | Huck et al. . | |
| 5,511,689 | 4/1996 | Frank . | |
| 5,685,833 | 11/1997 | Turngren . | |
| 5,782,786 | 7/1998 | Tomaiulo . | |
| 6,092,657 | * 7/2000 | Hopkins | ................................. 206/409 |
| 6,095,455 | * 8/2000 | Greer | .................................. 242/597.8 |

FOREIGN PATENT DOCUMENTS

| | | | |
|---|---|---|---|
| 937042 | * 9/1963 | (GB) | ....................................... 221/73 |
| 0028999 | * 1/1990 | (JP) | ........................................ 221/73 |

* cited by examiner

*Primary Examiner*—H. Grant Skaggs
(74) *Attorney, Agent, or Firm*—Joel D. Myers; Myers & Associates, Intellectual Property Law, P.C.

(57) ABSTRACT

A bandage dispensing device having a handle portion and a head portion. The handle portion comprises a plurality of finger indentions formed on the exterior front portion of the handle to facilitate the gripping of the device. The head portion, attached at the upper portion of the handle, comprises a clip formed on the rear exterior of the head to removably attach the device to a portion of a person's clothing. To incrementally advance a bandage assembly, the interior of the head portion generally comprises a rotatable spool of a bandage assembly strip, a drive belt, and a means for advancing said drive belt incrementally. The strip of bandage assembly comprises spaced apart bandages carried by a nonadhering carrying strip having preferably one throughhole formed between each bandage, wherein pins perpendicularly extending from the drive belt engage within a plurality of the throughholes. A push button extends generally to the exterior of the device at the top of the head portion to allow easy contact with the user's thumb and is in mechanical communication via an advancing mechanism with the drive belt. As the push button is pushed, the advancing mechanism rotates the drive belt in the counter-clockwise direction by one increment. Upon release of the button, a spring urges the assembly back to its original position, however, the advancing mechanism disengages from the drive belt and moves back to its original position without rotating the drive belt in the clockwise direction.

15 Claims, 2 Drawing Sheets

BANDAGE DISPENSING DEVICE

TECHNICAL FIELD

The present invention relates generally to bandage dispensing devices, and, more specifically, to a portable push-button device for dispensing bandages.

BACKGROUND

Bandages are one of the most widely utilized first aid supplies available. Bandages are typically used to decrease prolonged loss of body fluids by covering and protecting a multitude of skin transgressions such as open wounds, surgical incisions, venipuncture/IV insertions, post injection punctures, abrasions and burns. As such, in typical medical facilities, especially hospitals, bandages may be applied hundreds of times per day.

Unfortunately, however, the prior art method of applying a bandage to a target area often requires the use of two hands and is relatively time consuming, and thus, inefficient and costly. More specifically, when the need for a bandage arises, a nurse or doctor must first retrieve a bandage from a storage cabinet and/or storage room thereby requiring retrieval time and effort on behalf of the nurse or doctor. Then a bandage covering must be removed to expose the bandage. Next, typically two adhesive coverings must be removed to expose the adhesive portion of the bandage, wherein the bandage can then be secured over the target area. Because these steps are performed numerous times each day at numerous health facility locations by numerous nurses and doctors, many hours in any given day are consumed performing these simple yet necessary tasks.

In an attempt to remedy these inefficiencies, a multitude of bandage dispensers have been proposed. Examples of such devices may be found by reference to U.S. Pat. No. 5,511,689 to Frank; U.S. Pat. No. 5,499,740 to Huck et al.; U.S. Pat. No. 5,358,140 to Pellegrino; U.S. Pat. No. 5,271,522 to Ko et al.; U.S. Pat. No. 5,065,894 to Garland; U.S. Pat. No. 4,735,342 to Goldstein; U.S. Pat. No. 4,872,593 to Behringer; and U.S. Pat. No. 3,189,219 to Holzworth et al. However, in light of the present invention, these devices are disadvantageous. For instance, the patents to Holzworth et al., Huck et al., Pellegrino, Ko et al. and Goldstein all require that each bandage be pulled therefrom by hand and therefore, do not provide a means for advancing to the next bandage without physical contact with the previous bandage. Although the patents to Behringer, Garland and Frank provide a means for advancing to the next bandage without contact with the previous bandage, said means are inefficient. For instance, Frank and Behringer disclose devices that allow the bandages to be advanced via a rotating crank or knob. Not only can these advancement means interfere with other on-going procedures, they can easily be inadvertently rotated. Moreover, none of the above references can be easily attached to a person's clothing to provide an ambulatory bandage dispenser nor do they provide hand gripping means to facilitate one hand operations for larger wounds requiring more than one bandage.

It is therefore readily apparent that a new and improved device for dispensing bandages is needed that can be attached to a person's clothing and provide a simple advancing mechanism to allow push button advancement and thus one-handed operations. It is, therefore, to the provision of such an improvement that the present invention is directed.

BRIEF SUMMARY OF THE INVENTION

Briefly described, in a preferred embodiment, the present invention both overcomes the above-mentioned disadvantages, and meets the recognized needs for such device, by providing a bandage dispensing device having means for attaching the device to a person's clothing such that the device is portable and easily accessible.

The present invention generally comprises a relatively hollow casing formed in a generally 7-shape having a handle portion and a head portion. The handle portion preferably comprises a plurality of finger indentions formed on the exterior front portion of the handle to facilitate the gripping of the device. The head portion, attached at the upper portion of the handle, generally comprises an attachment means such as a clip formed on the rear exterior of the head to removably attach the device to a portion of a person's clothing. Formed at the front exterior of the head are preferably two apertures, an exit aperture and an reentry aperture, wherein a bandage assembly exits the interior of the device through the exit aperture, thereby allowing a bandage carried by the bandage assembly to be removed, and then the remaining bandage carrying strip reenters the interior of the device through the reentry aperture. A second exit aperture is formed on the chin of the head portion, wherein the bandage carrying strip is channeled therethrough such that the strip extends downward away from the front portion of the head to ensure that the strip does not interfere with bandage removal.

To provide a means for incrementally advancing the bandage assembly, the interior of the head portion generally comprises a rotatable spool of a bandage assembly strip, a drive belt, and a means for advancing said drive belt incrementally. The strip of bandage assembly generally comprises spaced apart bandages carried by a nonadhering carrying strip having preferably one throughhole formed between each bandage, wherein pins perpendicularly extending from the drive belt engage within a plurality of the throughholes. A push button extends generally to the exterior of the device at the top of the head portion preferably more toward the rear of the device to allow easy contact with the user's thumb and is in mechanical communication with the drive belt.

The advancing mechanism preferably comprises an extension arm, a linkage arm and a one-direction engaging gear. As the push button is pushed, the extension arm is lowered thereby lowering the attached linkage arm thus rotating the drive belt in the counter-clockwise direction by one increment. Upon release of the button, a spring urges the assembly back to its original position, however, the engaging gear disengages from the drive belt and rotates back to its original position without rotating the drive belt in the clockwise direction.

A removable access door is formed preferably at the top of the head portion to provide a means for accessing the interior thereof to replace the roll of bandages and/or to make repairs to the interior mechanisms.

Thus, a feature and advantage of the present invention is to provide a new and improved portable bandage dispensing device that can be easily attached to a person's clothing to provide a readily accessible portable bandage dispenser.

A feature and advantage of the present invention is to provide a new and improved portable bandage dispensing device having a push button advancement means to facilitate one-hand advancement without the touching the bandage.

A feature and advantage of the present invention is to provide a new and improved portable bandage dispensing device having a plurality of finger indentions for facilitating the gripping of the device.

A feature and advantage of the present invention is to provide a new and improved portable bandage dispensing device that is generally 7-shaped to facilitate the application and dispensing of bandages.

A feature and advantage of the present invention is to provide a new and improved portable bandage dispensing device that can dispense bandages and apply one to a target area while eliminating or reducing the need for contacting the bandage by the user and therefore, reduces the spread of infections.

A feature and advantage of the present invention is to provide a new and improved portable bandage-dispensing device that is lightweight and thus easy to transport.

A feature and advantage of the present invention is to provide a new and improved portable bandage-dispensing device that is simple and inexpensive to manufacture.

These and other objects, features and advantages of the present invention will become more apparent to one skilled in the art by reference to the following detailed description of the preferred and alternate embodiments, the appended claim, and the accompanying drawings.

BRIEF DESCRIPTION OF THE FIGURES

The present invention will be better understood by reading the Detailed Description of the Preferred Embodiment with reference to the accompanying drawing figures, in which like reference numerals denote similar structure and refer to like elements throughout, and in which.

DETAILED DESCRIPTION OF THE PREFERRED EMBODIMENT

Figure 1:
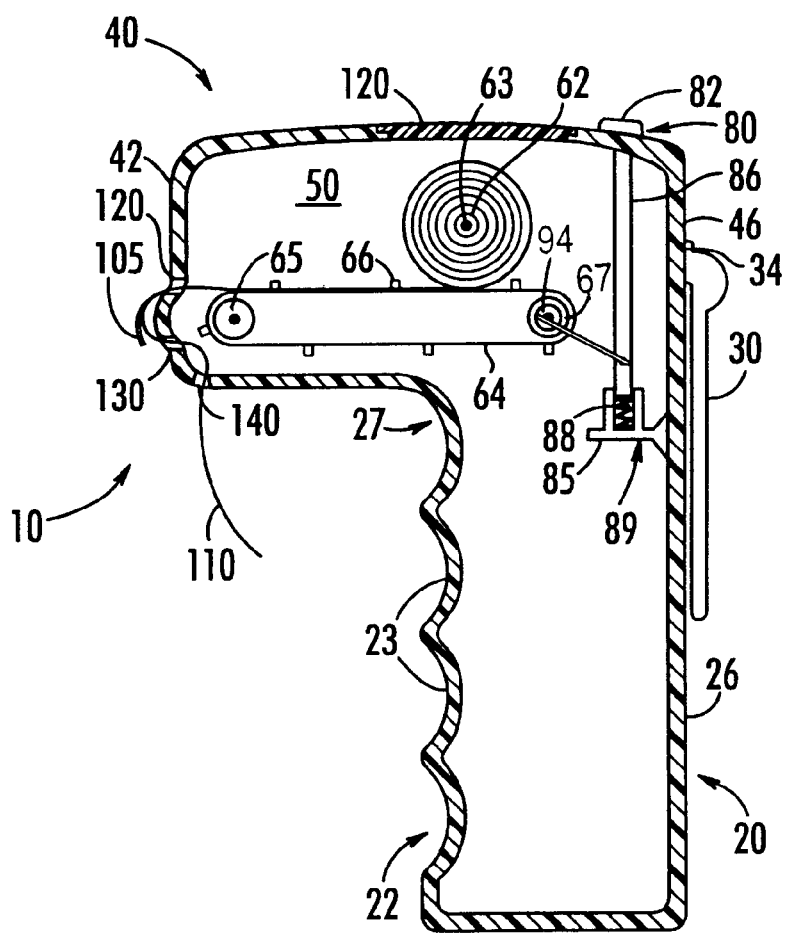
FIG. 1 is a side sectional view of the device according to a preferred embodiment of the present invention.
Figure 2:
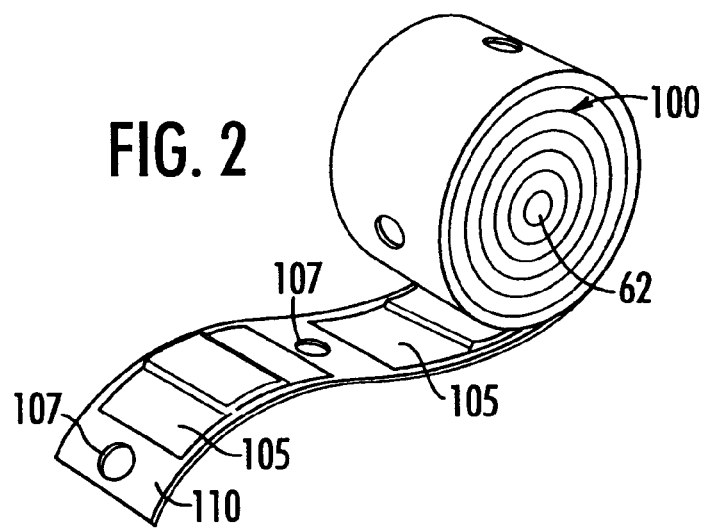
FIG. 2 is a perspective view of the bandage assembly according to a preferred embodiment of the present invention.

In describing the preferred and alternate embodiments of the present invention illustrated in the figures, specific terminology is employed for the sake of clarity. The invention, however, is not intended to be limited to the specific terminology so selected, and it is to be understood that each specific element includes all technical equivalents that operate in a similar manner to accomplish similar functions.

With regard to all such embodiments as may be herein described and contemplated, it will be appreciated that optional features, including, but not limited to, aesthetically pleasing coloration and surface design, and labeling and brand marking, may be provided in association with the present invention, all without departing from the scope of the invention.

Device 10 is generally a "7"-shaped portable push button bandage dispenser. More specifically, device 10 comprises handle portion 20 and head portion 40, wherein head portion 40 is connected to and extends generally perpendicular from upper portion 27 of handle portion 20. Preferably, handle portion 20 and head portion 40 are hollow such that cavity 50 is formed therein for containing dispensing mechanism 60 and to reduce the overall weight of device 10. However, in an alternate embodiment, handle portion may be solid. Handle portion 20 is generally a rectangular-shaped member having a grip portion 22 and a rear portion 26 wherein grip portion 22 comprises a plurality of finger indentions 23 dimensioned for receiving the fingers of the user's hand. Head portion 40 also has a generally rectangular profile wherein the rear 46 of head portion 40 is generally vertically aligned with the rear 26 of handle portion 20, and wherein the front 42 of head portion 40 preferably extends forward and beyond the front 22 of handle portion thereby forming the generally "7"-shaped profile.

To provide a means for attaching device 10 to a belt or other portion of the user's clothing, clip 30 is generally attached at the rear 46 of head portion 40 and extends generally downward to the rear 26 of handle portion 20. Clip 30 is connected via connection point 34 and is made of sufficiently flexible materials such as metal or plastic to allow the lower portion of the clip to flex outward to allow the insertion of a belt or other article of clothing. Connection point 34 can be any one of many known connection means such as a screw or bolt, or it can be molded as an integral part of head portion 40.

To dispense a bandage 105, dispensing mechanism 60 is attached within cavity 50 of head portion 40 to one of the side walls of head portion 40. Dispensing mechanism 60 generally comprises bandage spool 62, bandage assembly 100, drive belt 64 and first and second drive gears 65 and 67, respectively. Bandage assembly 100 comprises carrying strip 110, bandage 105 carried on carrying strip 110, and pin holes 107 spaced generally evenly and between each bandage 105. To provide a means for gripping bandage assembly 100, a plurality of preferably evenly spaced pins 66 extend outwardly from drive belt 64 and engage within pin holes 107 in bandage assembly 100. An elongated section of bandage assembly 100 is wrapped around spool 62, wherein spool 62 is rotatably and removably connected to the casing of head portion 40 via rod 63. Rod 63 preferably snap fits within a center throughhole formed in spool 62 such that when all bandages 10 are used, a slight hand force will unsnap spool 62 from rod 63 to allow replacement with a new spool 62 having a plurality of rolled unused bandages 105 thereon. The snap fitting between spool 62 and rod 63 can be a ball-and-bearing fitting, an indention-protrusion fitting or other known snap fittings.

Drive belt 64 and first and second drive gears 65, 67 are generally positioned at the lower portion of head portion 40 preferably below and to the front of bandage spool 62. Drive gears 65, 67 are preferably positioned perpendicular to exit aperture 120. Bandage assembly 100 is then channeled over the top of drive belt 64 with pins 66 inserting within pin holes 107 and then extending out head portion 40 at first exit aperture 120. After bandage assembly 100 exits the interior of device 10 through first exit aperture 120, thereby allowing the removal of a bandage 105 therefrom, the remaining carrying strip 110 is redirected back through reentry aperture 130 located in the front 42 of head portion 140 below and proximal to first exit aperture 120, and then exiting again the interior of device 10 at second exit aperture 140 located at surface 43 of head portion 40. As such, because of the relatively sharp angle of return from first exit aperture 120 to reentry aperture 130, bandage 105 separates from bandage assembly 100 to allow the removal and application of bandage 105 by simply contacting or pressing the bandage 10 onto the target area, thus eliminating or reducing the need for user contact with bandage 105, thereby ultimately reducing the likelihood of contamination and spread of infections. In an alternate embodiment, a one way trap (not shown) can be attached to second exit aperture 140 to prevent carrying strip 110 from inadvertently being pulled back into W device 10 after carrying strip 110 exits through second exit aperture 140. In an alternate embodiment, perforations (not shown) are formed on carrying strip 110 between each bandage 105 to facilitate the separation of carrying strip 110 with bandage 105 from the remaining bandage assembly 100. This alternate embodiment may be utilized when it is preferred to maintain bandage 105 intact with carrying strip 110 (i.e., when bandage 105 is not being immediately applied to a target area.

To provide incremental advancement of drive mechanism 60, a push button advance mechanism 80 is provided. Push button advance mechanism 80 generally comprises push button 82 and linkage means 84, wherein linkage means 84 is in mechanical communication with drive belt 64 such that when push button 82 is pushed, linkage mechanism 84 causes drive belt and/or drive gears 65, 67 to incrementally advance by one bandage 105 on bandage assembly 100. Linkage means 84 can be a plurality of many known linkage mechanisms within the art. However, linkage mechanism 84 preferably comprises extension arm 86, spring 88, spring support 89, linkage arm 90 and linkage gear 94. Extension arm 86 is connected to and generally extends downward from push button 82 with spring 88 connected to and acting on the bottom of extension arm 86 to urge extension arm 86 and thus button 82 in the upward direction to its original position. The lower end of spring 88 rests within and is held in a fixed position by spring support 89. Spring support 89 provides a channel 87 having a lower wall 85 for receiving and supporting spring 88, and is generally mounted to the rear 26 of handle portion 20 or to the rear 46 of head portion 40.

One end of linkage arm 90 is attached to the lower portion of extension arm 86 with the other end of linkage arm 90 attached to linkage gear 94 wherein linkage gear 94 is attached to and generally parallel with drive gear 67, and wherein linkage gear 94 preferably has the same axis of rotation as drive gear 67. Linkage gear 94 is preferably a commonly well-known one directionally engaging mechanism, typically found in ratchet-type tools, wherein linkage gear 94 only engages drive gear 67 in the counter-clockwise direction. In other words, when push button 82 is pushed downward, linkage arm 90 pulls linkage gear 94 such that it rotates in the counter-clockwise direction, thus causing drive gear 67 to rotate in the counter-clockwise direction thereby advancing the bandage assembly 100. When push button is released, spring 88 urges push button upward back to its original position thus causing linkage arm 90 to push linkage gear 94 clockwise back to its original position; however, linkage gear 94 releases from drive gear 67 when rotated in the clockwise direction thus drive gear 67 does not rotate and remains in the advanced position. It should be noted that one skilled in the art can select the proper dimensions and angles of connection for linkage means 84 to ensure that one bandage 105 is incrementally advanced with each push of push button 82.

Figure 3:
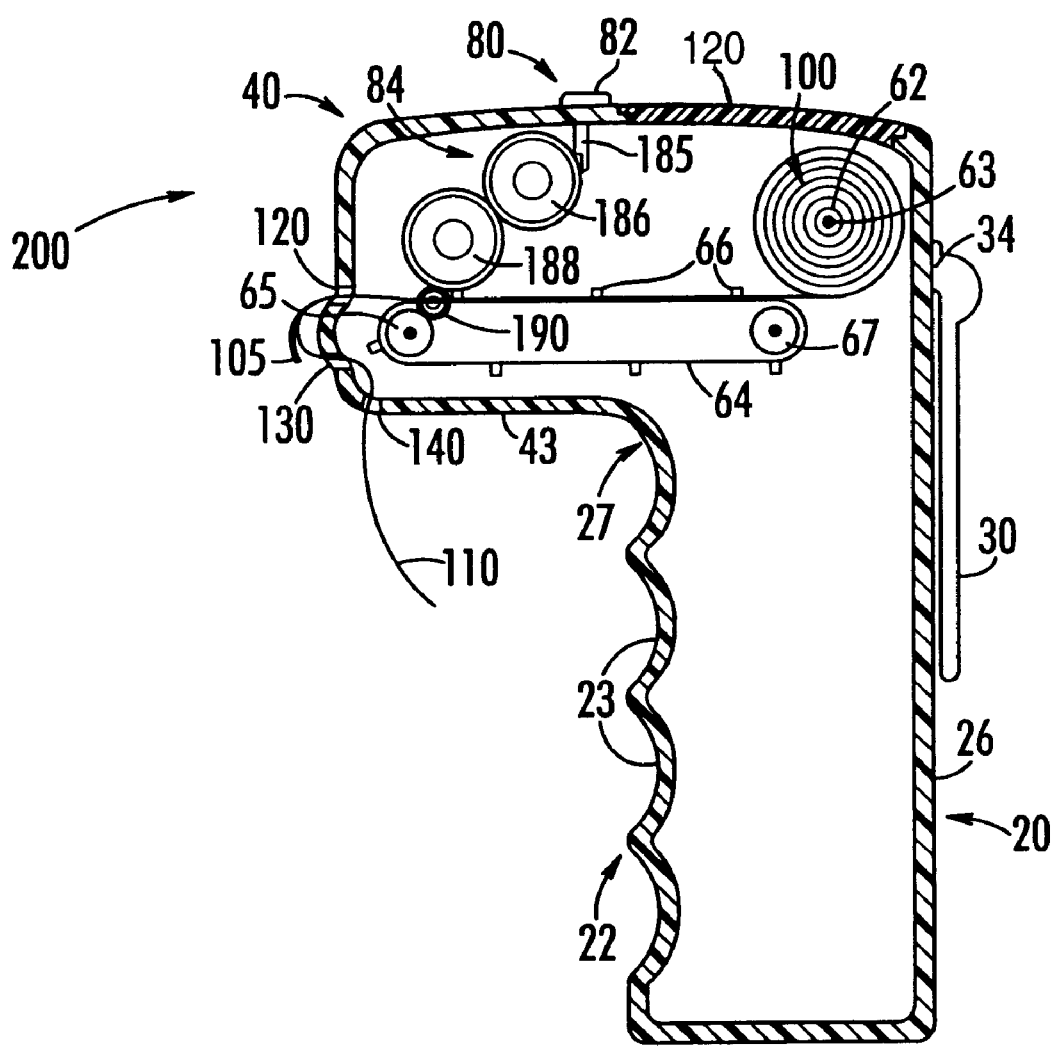
FIG. 3 is a side sectional view of the device according to an alternate embodiment of the present invention.

In alternate embodiment 200, as shown in FIG. 3, an alternate linkage mechanism 184 is shown. Alternate linkage mechanism 184 generally comprises first gear 186 connected to push button 82 via extension arm 185, second gear 188 in mechanical communication with first gear 186, and third gear 190 in mechanical communication with second gear 188 and drive gear 65, such that when push button 82 is pushed, first gear 186 rotates clockwise causing second gear 188 to rotate counter-clockwise causing third gear 190 to rotate clockwise and causing drive gear 65 to rotate counter-clockwise thereby advancing bandage assembly 100 by one bandage 105. It should be noted that one skilled in the art can select the proper dimensions and gear ratios for linkage means 84 to ensure that one bandage 105 is incrementally advanced with each push of push button 82.

To allow entry into cavity 50 of device 10 and device 200 to replace spool 62, a removable access 120 is preferably formed in the top of head portion 40. In an alternate embodiment, access 120 may be formed on the side of head portion 40.

It should be noted that although a single molded unit for device 10 is preferred, two halves may be joined together to form device 10. In addition, although the "7"-shaped profile is preferred, other various shapes may be utilized. Drive belt 64 may also be driven by one drive gear in lieu of two. In an alternate embodiment, a tab (not shown) may be placed on the leading edge of bandage 105 to facilitate its removal from carrying strip 110.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

What is claimed is:

1. A device for dispensing bandages, wherein the bandages are carried by a carrying strip having a first end and a second end and wherein the bandages and the carrying strip are rolled onto a spool having an aperture formed therein, said device comprising:

a casing having at least one hollow section therein and at least one aperture;

a rotatable belt having a plurality of pins extending therefrom, said belt carried by said casing within said hollow section;

means carried by said casing for rotatably carrying the spool of bandages; and means carried by said casing for removably attaching said device to a user, wherein a plurality of throughholes are evenly spaced between said bandages such that at least one of said pins engages at least one of said throughholes and wherein the first end of the carrying strip extends through said aperture to the exterior of said casing such that a user can pull the first end of the carrying strip thus rotating the spool and thereby exposing additional bandages.

2. The device of claim 1, wherein said spool rotatable carrying means is a rod, said rod is dimensioned to engage the aperture formed in the spool.

3. The device of claim 1, wherein said attaching means is a clip.

4. The device of claim 1, further having a plurality of finger indentions formed in said casing to facilitate the gripping of said device.

5. A device for dispensing bandages, wherein the bandages are carried by a carrying strip having a first end and a second end and wherein the bandages and the carrying strip are rolled onto a spool having an aperture formed therein, said device comprising:

a casing having at least one hollow section therein and at least one aperture;

means carried by said casing for rotatably carrying the spool of bandages;

a rotatable guiding belt having a plurality of pins extending therefrom, said belt carried by said casing within said hollow casing;

means carried by said casing for incrementally advancing the bandages; and means carried by said casing for removably attaching said device to a user, wherein the first end of the carrying strip extends through said aperture to the exterior of said casing, wherein a plurality of throughholes are evenly spaced between said bandages such that at least one of said pins engages at least one of said throughholes, and wherein said advancing means advances at least one bandage through said aperture of said casing.

6. The device of claim 5, wherein said spool rotatable carrying means is a rod, said rod is dimensioned to engage the aperture formed in the spool.

7. The device of claim 5, wherein said attaching means is a clip.

8. The device of claim 5, further having a plurality of finger indentions formed in said casing to facilitate the gripping of said device.

9. The device of claim 5, wherein said advancing means is a push-button advancing means.

10. A device for dispensing bandages comprising:
   a casing having at least one hollow section therein, an exterior and at least one aperture;
   a spool removably and rotatably carried by said casing;
   a bandage assembly having a carrying strip, a plurality of evenly spaced-apart bandages carried thereon and a plurality of throughholes evenly spaced between said bandages such that at least one of a plurality of pins engages at least one of said throughholes,
   said carrying strip having a first end and a second end, said second end of said carrying strip and a portion of said carrying strip rolled onto said spool;
   a rotatable belt carried by said casing within said hollow section for guiding said carrying strip and said bandages from said spool through said aperture of said casing, said belt having a plurality of pins extending therefrom;
   means carried by said casing for incrementally advancing said bandages; and
   means carried by said casing for removably attaching said device to a user,
wherein said first end of said carrying strip extends through said aperture to said exterior of said casing, and wherein said advancing means advances at least one of said bandages through said aperture of said casing.

11. The device of claim 10, wherein said advancing means is a push-button advancing means.

12. The device of claim 11, wherein said push button advancing means engages said guide means and advances said guide means when said push button is pressed, thus advancing at least one of said bandages.

13. The device of claim 10, wherein said attaching means is a clip.

14. The device of claim 10, wherein said casing has generally a "7" shape.

15. The device of claim 10, further comprising finger indentions formed in said casing to facilitate the gripping of said device.

* * * * *